United States Patent [19]

Feuer et al.

[11] 4,324,743

[45] Apr. 13, 1982

[54] METHOD OF PREPARING GAMMA-L-GLUTAMYL TAURINE

[75] Inventors: László Feuer; Árpád Furka; Ferenc Sebestyén; Jolán Hercsel née Szepespataky; Erzsébet Bendefy née Dobay, all of Budapest, Hungary

[73] Assignee: Chinoin Gyógyszer és Vegyészeti Termékek Gyára Rt., Budapest, Hungary

[21] Appl. No.: 814,726

[22] Filed: Jul. 11, 1977

Related U.S. Application Data

[63] Continuation of Ser. No. 571,766, Apr. 25, 1975, abandoned.

[30] Foreign Application Priority Data

Apr. 29, 1974 [HU] Hungary ............................. FE 928
Mar. 26, 1975 [HU] Hungary ............................. CI 1558

[51] Int. Cl.$^3$ ............................................. C07C 143/02
[52] U.S. Cl. ................................................. 260/513 N
[58] Field of Search ..................... 260/501.12, 513 N

[56] References Cited

U.S. PATENT DOCUMENTS

| | | | |
|---|---|---|---|
| 3,384,662 | 5/1968 | Höllinger et al. | 260/501.12 |
| 3,645,996 | 2/1972 | Southard | 260/501.12 |
| 3,706,790 | 12/1972 | Sprague et al. | 260/501.12 |
| 3,763,232 | 10/1973 | Kaiser et al. | 260/501.12 |
| 3,852,338 | 12/1974 | Kaiser et al. | 260/501.12 |
| 3,943,173 | 3/1976 | Colella et al. | 260/501.12 |
| 3,954,783 | 5/1976 | Scherberich | 260/501.12 |

OTHER PUBLICATIONS

Boissonnas, "Advances in Org. Chem.", vol. 3, pp. 159–190, (1963).

*Primary Examiner*—Alan Siegel
*Attorney, Agent, or Firm*—Karl F. Ross

[57] ABSTRACT

A process for preparing gamma-L-glutamyl-taurine, which has been found to be effective therapeutically through the control of vitamin A metabolism, which comprises reacting carbobenzyloxy-L-glutaminic acid-α-benzyl ester with triethylamine and isobutylchloroformate and then treating the reaction mixture with cystamine dihydrochloride to recover N,N'-bis-(N-carbobenzyloxy-gamma-[α-benzyl]-L-glutamyl)-cystamine. The latter is reacted with hydrogen peroxide in glacial acetic acid to produce carbobenzyloxy-gamma-(α-benzyl)-L-glutamyl taurine. The latter compound is treated with hydrogen bromide in glacial acetic acid to recover the gamma-(α-benzyl)-L-glutamyl taurine and this compound is treated with potassium hydroxide solution to yield the gamma-L-glutamyl taurine.

3 Claims, No Drawings

METHOD OF PREPARING GAMMA-L-GLUTAMYL TAURINE

This is a continuation of application Ser. No. 571,766, filed Apr. 25, 1975, now abandoned.

This invention relates to novel amino acid derivatives and pharmaceutical compositions containing the same, as well as to a process for the preparation thereof.

The novel compounds according to the invention correspond to the general formula (I)

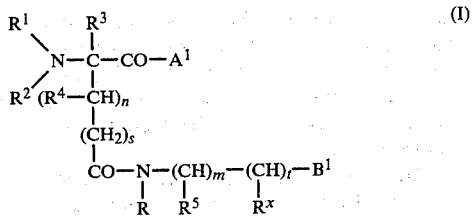

wherein $A^1$ stands for hydroxy, $C_{1-4}$ alkoxy, cycloalkoxy, aralkoxy, substituted aralkoxy, aryloxy, substituted aryloxy or a group of the general formulae $-NR_2^{14}$ or

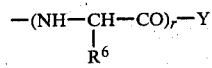

wherein $R^{14}$ is hydrogen, $C_{1-4}$ alkyl or aralkyl, $R^6$ is hydrogen, $C_{1-5}$ alkyl, aralkyl, hydroxy-substituted aralkyl, heteroaralkyl or a group of the general formula

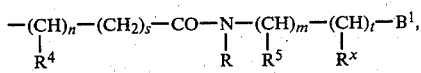

Y is hydroxy, amino, alkylamino, dialkylamino, $C_{1-4}$ alkoxy or aralkoxy, and r is an integer of from 1 to 10 or an average polymerization grade of up to 2000, $B^1$ is a group of the formulae $-SO_2OH$, $-OSO_2OH$, $-O-PO(OH)_2$ or $-S-S-R^{11}$, wherein $R^{11}$ is $C_{1-4}$ alkyl, aralkyl or aryl or a residue obtained when removing group $B^1$ from the general formula (I), R stands for hydrogen, $C_{1-4}$ alkyl or aralkyl, $R^x$ stands for hydrogen or halogen, $R^1$ stands for hydrogen, $C_{1-4}$ alkyl, aryl, aryl having a nitro or alkoxy substituent, aralkyl, substituted aralkyl, alkoxycarbonyl, aralkoxycarbonyl, aralkoxycarbonyl having a halogen, alkoxy, nitro, phenylazo or alkoxyphenylazo substituent, alkyl-substituted aryloxycarbonyl, acyl, benzoyl, arylsulfonyl, or

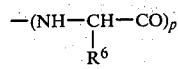

group (wherein $R^6$ has the same meanings as defined above and p is an integer of from 1 to 10 or an average polymerization grade of up to 2000), or a $-CO-$ group, $R^2$ stands for hydrogen, $C_{1-4}$ alkyl, aralkyl or a $-CO-$ group, but if $R^1$ and $R^2$ each stand for a $-CO-$ group, they form a ring through an o-phenylene, alkylene or $-CH=CH-$ group, $R^3$ stands for hydrogen, carboxy or carbalkoxy, $R^4$ stands for hydrogen, halogen, $C_{1-4}$ alkyl or hydroxy, $R^5$ stands for hydrogen, halogen, $C_{1-4}$ alkyl, carboxy, carboxamido, carbalkoxy or carboaralkoxy, m is 1, 2 or 3, n is 1, 2, 3 or 4, s is 0, 1, 2, 3 or 4, and t is 1, 2 or 3.

The salts and optically active isomers of the above compounds are also included by the scope of the invention.

Certain novel compounds according to the invention possess valuable pharmaceutical properties, whereas other representatives can be used as intermediates in the production of compounds with valuable physiological or pharmaceutical properties.

Concerning its biological activities, an outstandingly advantageous representative of the new compounds according to the invention is gamma-L-glutamyl-taurine of the formula

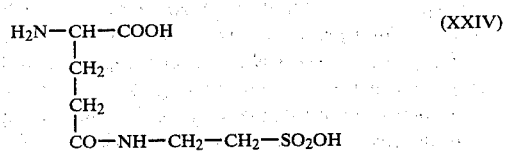

This compound possesses wide therapeutical and preventive effects on pathological alterations connected directly or indirectly with the injuries of the "AGAS" (Aerobiospherical-Genetical-Adaptational-System).

To elucidate the notion of the AGAS, the most important tissues and organs which constitute the system will be enumerated.

(a) Biological interfaces forming the boundary between the organism and the atmosphere as biosphere (skin and other dermal structures, cornea and conjuctiva, mouth and pharyngeal cavity, respiratory tract and lungs);

(b) the skeletal system and the extremities (tubular and spongious bones, ball joints, the synovial membrane, skeletal musculature);

(c) the organs participating in the regulation of terrestrial ion balance (the transepithelial transport system, intestinal villi and renal tubules);

(d) the required thekodont teeth for the disintegration of solid food (with tooth bed and fixed by the root);

(e) terrestrial hearing, smelling and sound-forming organs.

The compounds prepared according to the present invention exert a biologically favourable therapeutic influence on the organs of the above system, as well as on the tissues thereof.

Furthermore, still in connection with the AGAS system, the compounds according to the invention exert the following effects:

Radioprotective effect, effect promoting wound healing, general mensenchyma activation effect, protection against the increased danger of the infections and contaminations of the mucous membrane and skin (the lysozyme production of the wet mucous membrane, development of ciliated epithelium in the respiratory tract, etc.), increased protection against the viral and fungal infections of the skin.

Against the significantly increased stress effects of terrestrial life (e.g. meteorological and vigorous diurnal alterations, increased danger of injury) the compounds tend to stabilize the adaptational syndrome, by preventing simultaneously damages in the peripheral tissue caused by glucocorticoids (e.g. damages in the connective tissues, in the bone matrix, etc.)

The development of immunohomeostasis (the increased recognition of the self and non-self cells).

The compounds according to the invention exert their activities in part directly, and in part through the control of the vitamin A metabolism by the production of more polar vitamin A metabolites. This activity is similar to that exerted by parathormone on the 25-hydroxy-cholecalciferol-1-α-hydroxylase enzyme of the renal tubules. The above facts explain the wide and diverse biochemical, pharmacological and therapeutical activities of the compounds according to the invention.

(A) Effects of vitamin A character:

(a) Pharmacological and biochemical effects:

Effect promoting the incorporation of labelled sulfate in the cartilage of rats, and in the eye lens, the liver and lung tissues of chicken embryo; effect promoting the incorporation of labelled phosphorous in the cartilage of rats; effect promoting the synthesis of chondroitidinsulfate; effect favourably influencing wound healing, even decreased wound healing caused by cortisone administration in rats and dogs; effect increasing mastocyte degranulation; vitamin A potentiating effect in the case of experimental hypo- or hypervitaminosis on rats and chickens; moderation effect on the stress ulcer on rats; effect increasing lysosyme production; effect influencing the trace element turnover (silicon, copper, zinc, manganese, fluorine); effect promoting the epithel formation; effect increasing the alkaline phosphatase activity; effect exerted on the formation of pouch induced by the local effect of vitamin A; a very flat run of the dose-response curve, and a change in premonitory sign for high doses effect activating the Golgi apparatus; effect promoting the formation of goblet cells; effect increasing the concentration of serum vitamin A.

(b) Use in the clinical therapy:

Keratoconjunctivitis sicca; Sjögen's syndrome; rhino-laryngo-pharingitis sicca; ozaena; bronchitis chronica; synobronchitis; mucovisciodis; inclination of pheumopathies of the childhood; paradontosis; increased disposition of the skin and the mucous membrane to infections of viral and fungal origin; cortisonantagonism; operation wounds and injuries of the mucous membrane; erosio coli; pruritis group; disturbances of the taste and smell senses.

(B) Effects of no vitamin-A character:

(a) Pharmacological and biochemical effects: effect activating the Golgi apparatus; effect promoting the formation of goblet cells; effect increasing the concentration of serum vitamin A.

Transitory blood-sugar decreasing effect; effect increasing phosphaturia and decreasing serum phosphate level; radioprotective effect; in labyrinth tests at inactive animals a promoting effect on reaching the target; effect moderating experimental fluoro is and cadmium intoxication; effect decreasing the experimental lathyrism symptoms; effect increasing the cyclic adenosine-monophosphate excretion of the kidney; effect increasing enzyme activity of the liver tyrosine-aminotransferase.

(b) Use in the clinical therapy:

less serious irradiation injuries; vitiligo; muscle hypotony; psychoenergetizing effect; effects favourably influencing the involutional, gerontological states and the mnestic functions; cheloid disposition; spondylosis ankylopoetica; diseases of the locomotive organs of detritional origin; sclerotic fundus; amyloidosis; morphea; mastopathya fibrocystica.

The durations of the treatment with the compounds according to the invention are widely different. Upon an oral dose of 5 μg. of the chemically pure active substance administered three times a day some of the patients become symptom-free already after two weeks (e.g. in the case of rhino-laryngo-pharyngitis sicca), for the treatment of certain diseases one to two months are needed (e.g. parodontosis, Sjögren's syndrome), whereas in the case of other diseases treatment periods of three to six months are required (e.g. spondylosis ankylopoetica).

The compounds according to the invention can be converted into cosmetical or pharmaceutical compositions for use in the human or veterinary therapy. These compositions may contain the compounds according to the invention as the sole active ingredient or in combination with other biologically active substances. The active agents according to the invention are administered preferably three times a day in dosages of 50 to 500 nanograms/kg. body weight.

One tablet contains 2 to 20 micrograms, preferably about 10 micrograms of the active ingredient admixed with biologically inert carriers (e.g. lactose, starch) and usual auxiliary substances (e.g. granulating agents and lubricants, such as polyvinyl pyrrolidone, gelatine, talc, magnesium stearate, ultrafine silica, etc.). Taking into consideration the very low dose, to obtain an even dispersion of the active substance in the tablet it is preferable to admix the active principle in the form of solution with the tablet mass prior to granulation and to prepare a homogeneous mixture using a kneeding machine. The required very low effective dosage permits to prepare the active principle at a large laboratory scale, even for the production of several billions of tablets, at an acceptable price. The active principle is stable and therefore the tablets can be stored for long time. The active principle content of depot tablets or spansuled capsules may be between 10 to 30 μg.

Injectable preparations containing the active principle in powder ampoules optionally in admixture with a biologically indifferent water-soluble diluent contain preferably 5 to 10 μg. of active principle per ampoule. The parenteral application may be intramuscular, subcutaneous or intravenous. The active principle in the given concentrations does not irritate the tissues or vessel walls, and can be applied in the form of infusion as well.

Suppositories can be prepared with an active principle content of 2 to 20 μg., preferably 10 μg., using cocoa butter or any synthetic wax or fat (e.g. Imhausen mass, GFR) applicable for this purpose.

Ointments for dermatological or cosmetic purposes prepared with the usual hydrophilic or hydrophobic ointment bases (e.g. cholesterol, paraffine, glycerine, lanoline, linseed oil, etc.) may have an active principle content of 0.1 to 1.0 μg./g.

Aerosol preparations may contain the active principle in a concentration of 0.1 to 1.0 μg./g. Perlingual tablets may have an active principle content of about 10 μg. per tablet and a degradation time of 0.5 to 1 hour.

The polymers with high molecular weights having sustained effect can also be prepared e.g. in the form of suspensions with an active principle content of 1 to 5 μg./g. Similarly, injectable preparations with sustained effect can be prepared from the polymers or from the salts of the compounds according to the invention with organic bases of high molecular weights (e.g. protamine, histone). These compositions may contain the active principle in an amount of 10 to 20 μg. per ampoule.

The dermatological and cosmetic powders may have an active principle content of 0.1 to 1 μg./g., and contain the usual carriers (e.g. talc).

Eye drops applied for ophthalmologic purposes and the ointments miscible or immiscible with tear have an active principle content of 0.1 to 1.0 μg./g.

For peadiatric purposes the most preferred dosage is 0.3 μg. of active principle per kg. of body weight.

All sterile compositions are prepared preferably by sterile filtration.

Several combinations of the above preparations containing the compounds according to the invention increase, supplement or modify the desired preventive, therapeutical or cosmetic effect. Primarily, the following combinative supplementary components should be mentioned:

Vitamin A, vitamin C, vitamin E, vitamin K, trace elements, cortisone and its derivatives, progesterone, hormones of the thyroid gland, products of radiomimetic and immunosuppressive effects, psychopharmacons (especially tranquillizers or thymoleptics), organic silicon compounds, gerontological preparations, oral antidiabetics, antiphlogistics antihistamines, etc. The dosage of the components in the combination is generally identical with the usual therapeutical dosages when using them independently.

The compounds according to the invention can be applied furthermore as additives in therapeutical and nutrient premixes. Used in such compositions the compounds increase the weight gain and decrease the vitamin A demand and/or increase the absorption and metabolism of vitamin A. The compounds improve the absorption and increase the blood level of trace elements. When used as feed additive, they can be administered to the animals in a daily oral dosage of 100 to 300, preferably about 200 nanograms/kg. body weight. This corresponds generally to a concentration of 1 to 2 μg. per kg. of feed (i.e. 1 to 2 mg./ton or 0.001 to 0.002 ppm) when admixed with the animal feed. Considering the very low concentration required, the compounds according to the invention can be admixed to vitamin premixes or microcapsules containing other valuable feed additives, or can be administered as an additive of the drinking water or the licking salt. The compounds according to the invention can also be used for veterinary purposes in forms similar to those applied in the human therapy (epithelization, wound healing, bone fractures, etc.).

It is a common structural characteristic of the compounds having the general formula (I) that they contain an α-substituted dicarboxylic acid moiety the ω-carboxy group of which is attached through an amido bond to a primary or secondary amino group containing in the alkyl side chain, beside other substituents, a strongly acidic group in the ω-position.

The compounds of the general formula (I) or their salts or optically active isomers can be prepared according to the invention as follows:

(a) if a compound of the general formula (I) containing a free primary amino group is to be prepared, the protecting group of a compound of the general formula (II)

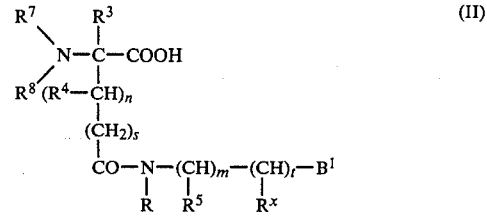

wherein $R^3$, $R^4$, $R^5$, $R^x$, R, $B^1$, n, m, s and t each have the same meanings as defined above and $R^7$ stands for aralkyl, formyl, trifluoroacetyl, p-toluenesulfonyl or —CO— group or a group of the general formulae $R^{15}$—OCO— or

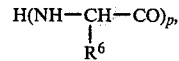

wherein p and $R^6$ each have the same meanings as defined above, and $R^{15}$ is $C_{1-4}$ alkyl, cycloalkyl, aralkyl, substituted aralkyl, aryl or substituted aryl, and $R^8$ stands for hydrogen or —CO—, but if $R^7$ and $R^8$ each stand for a —CO— group, they form a ring through an o-phenylene, alkylene or —CH=CH— group,
is split off by acidolysis, hydrogenolysis, treatment with dilute ammonium hydroxide, treatment with sodium, treatment with sodium amide, treatment with hydrazine, or enzymatic hydrolysis preferably using leucineaminopeptidase; or (b) if a compound of the general formula (I) containing a free carboxy group is to be prepared, a compound of the general formula (III),

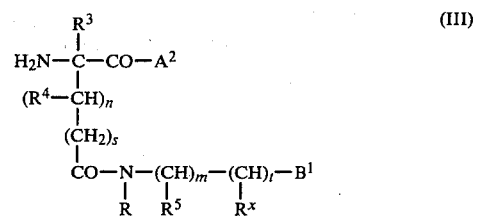

wherein R, $R^3$, $R^4$, $R^5$, $R^x$, $B^1$, n, m, s, and t each have the same meanings as defined above and $A^2$ stands for a $C_{1-4}$ alkoxy, aralkoxy or substituted aralkoxy group or a group of the general formulae —$NR_2^{16}$ or

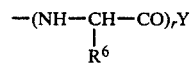

(wherein $R^6$, Y and r each have the same meanings as defined above, and $R^{16}$ is hydrogen, $C_{1-4}$ alkyl or aralkyl,
is subjected to saponification, acidolysis, hydrogenolysis or enzymatic hydrolysis; or (c) if a compound of the general formula (I) containing a free primary amino group and a free carboxy group is to be prepared, the protecting groups attached to the α-amino group and the α-carboxy group of a compound of the general formula (IV),

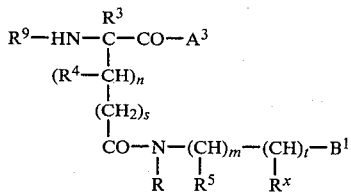

(IV)

wherein $R^3$, $R^4$, $R^5$, $R^x$, R, $B^1$, n, m, s and t each have the same meanings as defined above, $R^9$ stands for aralkyl, formyl, p-toluenesulfonyl or a group of the general formulae $R^{15}$—OCO— or

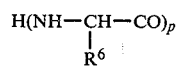

(wherein $R^{15}$, $R^6$ and p each have the same meanings as defined above), and $A^3$ stands for $C_{1-4}$ alkoxy, aralkoxy, substituted aralkoxy, or an aralkoxy, —$NR_2^{16}$ or

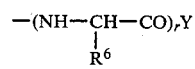

group attached to a solid polymer matrix, preferably to a styrene-divinylbenzene copolymer (wherein $R^{16}$, $R^6$, r and Y each have the same meanings as defined above), are split off simultaneously by acidolysis, alkaline hydrolysis, hydrogenolysis, treatment with sodium, treatment with sodium amide or enzymatic hydrolysis; or (d) if a compound of the general formula (I) containing sulfonyl, sulfonyloxy or phosphoryloxy group is to be prepared, a compound of the general formula (V),

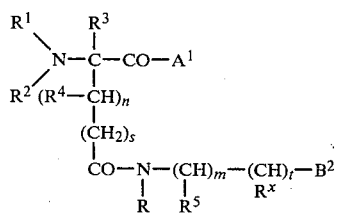

(V)

wherein $R^1$, $R^2$, $R^3$, $R^4$, $R^5$, $R^x$, R, $A^1$, n, m, s and t each have the same meanings as defined above and $B^2$ is halogen, hydroxy, p-toluenesulfonyloxy, or a group of the formulae —SH, —SO—OH or —$SO_2R^{10}$, wherein $R^{10}$ is $C_{1-4}$ alkoxy or aralkoxy, is oxidized, hydrolysed, reacted with an alkali sulfite or alkali bisulfite, or is esterified with sulfuric acid or phosphoric acid or with a derivative thereof; or (e) if a compound of the general formula (I) containing a sulfonyl group is to be prepared, a compound of the general formula (VI),

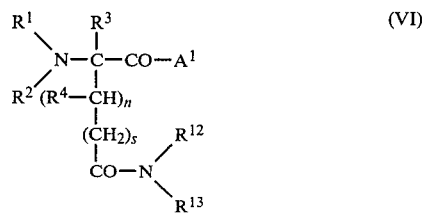

(VI)

wherein $R^1$, $R^2$, $R^3$, $R^4$, $A^1$, n and s each have the same meanings as defined above, $R^{12}$ stands for hydrogen, $C_{1-4}$ alkyl, aralkyl, or —$CH_2$—, and $R^{13}$ stands for alkali metal, vinyl group or —$CH_2$— group, but when $R^{12}$ and $R^{13}$ each represent —$CH_2$— group, they form together an aziridine ring, is alkylated with an alkanesulfonic acid or an alkali haloalkylsulfonate, or is reacted with sodium sulfite or sodium bisulfite; or (f) a compound of the general formula (VII),

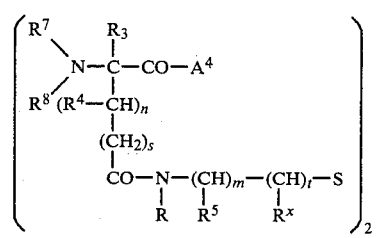

(VII)

wherein $R^3$, $R^4$, $R^5$, $R^7$, $R^8$, $R^x$, R, n, m, s and t each have the same meanings as defined above and $A^4$ is hydroxy, aralkoxy (preferably benzyloxy) or substituted aralkoxy (preferably p-methoxybenzyloxy or p-nitrobenzyloxy), is oxidized; or (g) if a compound of the general formula (I) containing a free primary amino group and a free carboxy group is to be prepared, a compound of the general formula (VIII),

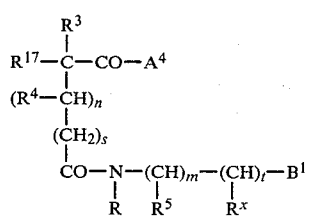

(VIII)

wherein $R^3$, $R^4$, $R^5$, $R^x$, R, $A^4$, $B^1$, n, m, s and t each have the same meanings as defined above, and $R^{17}$ stands for halogen, nitro, arylazo, substituted arylazo, hydrazo, monoarylhydrazo, diarylhydrazo, hydroxylamino or p-toluenesulfonyloxy, is reduced or reacted with ammonia; or (h) if a compound of the general formula (I) containing a free primary amino group and a free carboxy group is to be prepared, a compound of the general formula (IX),

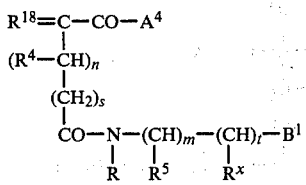 (IX)

wherein R, R⁴, R⁵, Rˣ, A⁴, B¹, n, m, s and t each have the same meanings as defined above, and R¹⁸ stands for oxyimino, imino, oxygen, or a group of the general formula =N—NH—R²⁰, wherein R²⁰ stands for hydrogen or aryl, is reduced, or is reacted with potassium cyanide and ammonia and subsequently hydrogenated, or is reacted with α-methylbenzylamine and subsequently hydrogenated; or (i) a compound of the general formula (X),

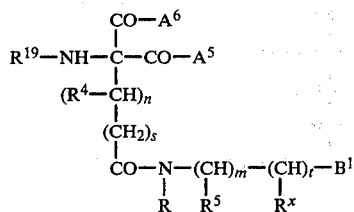 (X)

wherein R, R⁴, R⁵, Rˣ, B¹, n, m, s and t each have the same meanings as defined above, A⁵ stands for hydroxy, $C_{1-4}$ alkoxy or p-methoxybenzyloxy, A⁶ stands for hydroxy, $C_{1-4}$ alkoxy or p-methoxybenzyloxy, and R¹⁹ stands for hydrogen or a group of the general formula R¹⁵—OCO— (wherein R¹⁵ has the same meanings as defined above), is decarboxylated by reacting it with a hydrohalide, preferably with hydrogen bromide or (j) a compound of the general formula (XI), (XII), (XIII) or (XIV)

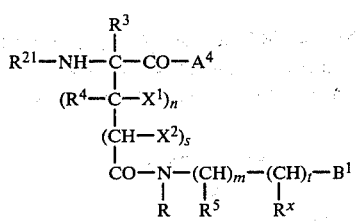 (XI)

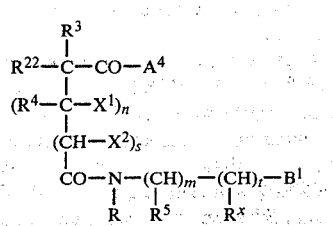 (XII)

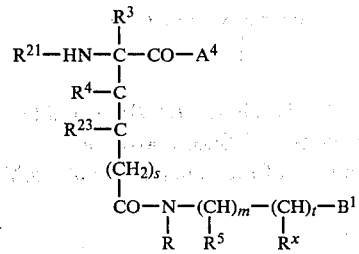 (XIII)

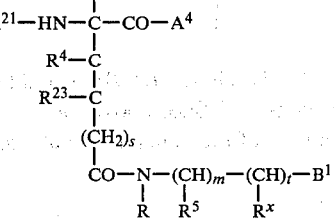 (XIV)

wherein R³, R⁴, R⁵, R, Rˣ, A⁴, B¹, n, m, s and t each have the same meanings as defined above, X¹ stands for hydrogen or halogen, X² stands for hydrogen or halogen, but at least one of X¹ and X² is always halogen, R²¹ stands for hydrogen, triphenylmethyl, benzyloxycarbonyl or substituted benzyloxycarbonyl, R²² stands for nitro, arylazo, substituted arylazo, hydrazo, monoarylhydrazo, diarylhydrazo or hydroxylamino, and R²³ stands for hydrogen, halogen, $C_{1-4}$ alkyl or hydroxy, is hydrogenated; or (k) if a compound of the general formula (I) containing a sulfonyl group is to be prepared, a compound of the general formula (XV)

$$\begin{matrix} & & O \\ & & \| \\ R^{24} & & C \\ \diagdown & & \diagup \diagdown \\ & N\text{—}CH & N\text{—}(CH)_m\text{—}(CH)_t\text{—}B^1 \\ \diagup & | & | \quad | \quad | \\ R^{25} & (R^4\text{—}CH)_n & R^5 \quad R^x \\ & | & \\ & (CH_2)_s & C=O \end{matrix}$$ (XV)

wherein R⁴, R⁵, Rˣ, B¹, n, m, s and t each have the same meanings as defined above, R²⁴ stands for hydrogen, $C_{1-4}$ alkyl, aryl, substituted aryl, aralkyl, acyl, arylsulfonyl, or a group of the general formula R¹⁵—OCO— (wherein R¹⁵ has the same meanings as defined above), and R²⁵ stands for hydrogen, $C_{1-4}$ alkyl or aralkyl, is subjected to partial hydrolysis, or (l) a compound of the general formula (XVI),

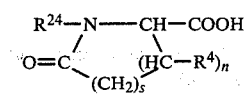 (XVI)

wherein R⁴, R²⁴, n and s each have the same meanings as defined above, is reacted with a compound of the general formula

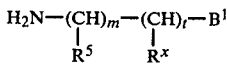

or a salt thereof, wherein $R^5$, $R^x$, $B^1$, m and t each have the same meanings as defined above; or (m) a compound of the general formula (XVII),

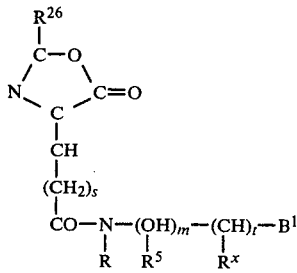

wherein R, $R^5$, $R^x$, $B^1$, s, m and t each have the same meanings as defined above, and $R^{26}$ stands for $C_{1-4}$ alkyl, aryl or aralkyl, is subjected to hydrogenation and partial hydrolysis; or (n) a compound of the general formula (XVIII),

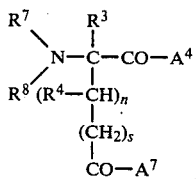

wherein $R^3$, $R^4$, $R^7$, $R^8$, $A^4$, n and s each have the same meanings as defined above and $A^7$ is hydroxy, azido, succinimidoxy, p-nitrophenoxy, pentachlorophenoxy, or $C_{2-4}$ alkoxycarbonyloxy, is reacted with a compound of the general formula (XIX)

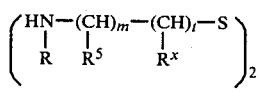

wherein R, $R^5$, m and t each have the same meanings as defined above; or (o) a compound of the general formula (XVIII), wherein $R^3$, $R^4$, $R^7$, $R^8$, $A^4$, $A^7$, n and s each have the same meanings as defined above, is reacted with a compound of the general formula (XX),

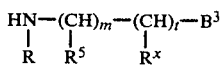

wherein R, $R^5$, $R^x$, m and t each have the same meanings as defined above and $B^3$ is a group of the formula $-SO_2OH$, $-OSO_2OH$ or $-O-PO(OH)_2$; or (p) the protecting group attached to the α-amino group of a compound of the general formula (XXI)

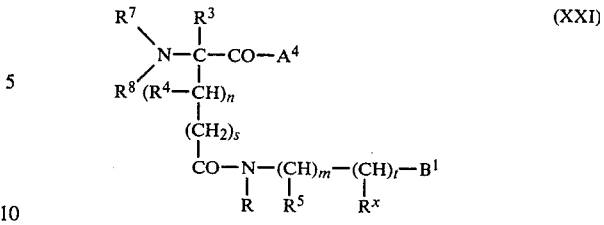

wherein $R^3$, $R^4$, $R^5$, $R^7$, $R^8$, $R^x$, R, $A^4$, $B^1$, m, n, s and t each have the same meanings as defined above, is split off; or (r) the protecting group attached to the α-carboxy group of a compound of the general formula (XXI), wherein $R^3$, $R^4$, $R^5$, $R^7$, $R^8$, $R^x$, R, $A^4$, $B^1$, m, n, s and t each have the same meanings as defined above, is split off; or (s) the α-amino group of a compound of the general formula (XXII),

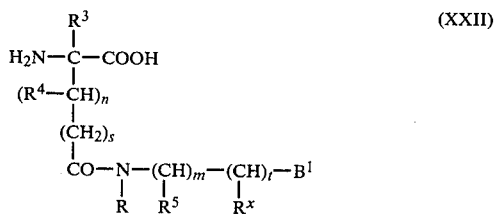

wherein $R^3$, $R^4$, $R^5$, $R^x$, R, $B^1$, m, n, s and t each have the same meanings as defined above, is acylated; or (t) the α-carboxy group of a compound of the general formula (XXII), wherein $R^3$, $R^4$, $R^5$, $R^x$, $B^1$, m, n, s and t each have the same meanings as defined above, is esterified; or (u) if a polymeric or oligomeric derivative of the general formula (XXIII)

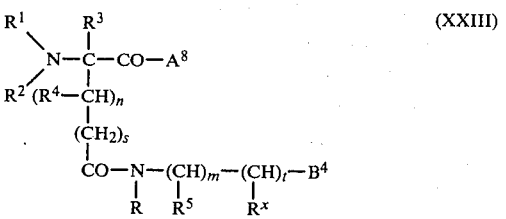

wherein $R^1$, $R^2$, $R^3$, $R^4$, $R^5$, $R^x$, R, m, n, s and t each have the same meanings as defined above, $A^8$ stands for a group of the general formula

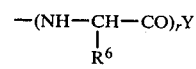

(wherein $R^6$, r and Y each have the same meanings as defined above), and $B^4$ is mercapto group or a group of the formula $-SO_2OH$, $-OSO_2OH$ or $-O-PO(OH)_2$, is to be prepared, an α-poly-amino-dicarboxylic acid-ω-activated ester is reacted with cysteamine, taurine or homotaurine; or (v) a polymeric or oligomeric derivative of the general formula (XXIII), wherein $R^1$, $R^2$, $R^3$, $R^4$, $R^5$, $R^x$, R, m, n, s, t, $A^8$ and $R^4$ each have the same meanings as defined above, is subjected to enzymatic hydrolysis preferably using carboxypeptidase or leucinaminopeptidase, optionally after the prior oxidation of the mercapto group; or (x) if a compound of the general formula (XXIII) is to be prepared, wherein $R^1$, $R^2$, $R^3$, $R^4$, $R^5$, $R^x$, R, m, n, s, t, $A^8$ and $B^4$ each have the same meanings as defined above, an ω-activated derivative of a peptide containing an α-amino-dicarboxylic acid is reacted with a compound of the general formula (XX), wherein R, $R^5$, $R^x$, $B^3$, m and t each have the same meanings as defined above; or (y) glutathione is subjected to partial hydrolysis, partial decarboxylation and oxidation, optionally after the previous protection of the α-amino and α-carboxy groups of the glutaminic acid moiety;

and, if desired, any of the thus-obtained compounds is converted into its salt or is liberated from its salt, and/or any of the above compounds is prepared in optically active form by using optically active reagents or by subjecting the obtained racemic product to resolution.

According to process variant (o) of the invention the compounds of the general formula (I) are prepared by forming an acid amide bond. In this case the appropriate α-amino-dicarboxylic acid derivative, with a protecting group or another substituent on the α-amino group and optionally also on the α-carboxy group, is coupled through the ω-carboxy group with e.g. 2-amino-ethanesulfonic acid, 3-amino-propanesulfonic acid, 2-phosphoethanolamine, 3-phospho-propanolamine or cysteinic acid. In this reaction a wide choice of protecting groups can be applied. The most preferred method of coupling is the "active ester" method. The formation and selective removal of the protecting groups, as well as the methods of coupling are described in detail by E. Schröder and K. Lübke ("The Peptides" Vol. 1: Methods of Peptide Synthesis, Academic Press, 1965).

Process variant (n) of the invention can be performed e.g. by acylating the amino group of cystamine or a substituted cystamine derivative with an α-amino-dicarboxylic acid derivative. Several coupling methods, such as the "active ester" or "mixed anhydride" methods can be used to perform the acylation. The product of this coupling reaction is reacted with hydrogen peroxide or a peracid, to yield the appropriate compound of the general formula (I) via the oxidative splitting of the disulfide bond (see process variant f/ of the invention).

According to process variant (d) of the invention an ω-amide of an α-amino-dicarboxylic acid is prepared first, wherein the ω-amine component contains another group in the place of the strongly acidic functional group. This latter group may be e.g. a sulfhydryl or sulfinic acid group. These compounds can be converted to the desired end-products by oxidation. If the functional group is halogen or p-toluenesulfonyloxy group (J. Chem. Soc. 1964, 824), these compounds can be reacted with an alkali sulfite or alkali bisulfite to yield compounds of the general formula (I) that contain sulfo groups. The intermediates containing hydroxy groups can be esterified to yield compounds of the general formula (I) that contain hydrosulfate or dihydrophosphate groups. If the intermediate contains a sulfonic ester group, this compound can be converted to the desired end-product of the general formula (I) by mild partial hydrolysis.

One can also use glutamine, asparagine or a substituted derivative thereof as starting material, the substituent being attached to a position other than the acid amide moiety. In this instance, according to process variant (e) of the invention, one of the acidic hydrogens of the acid amide group is replaced with e.g. metallic sodium, and the obtained compound is reacted with 2-bromo-ethanesulfonic acid or a salt thereof or with an alkanesulfonic acid to yield the respective compound of the general formula (I). As starting substances the ω-vinylamides or the ω-aziridine derivatives of the appropriate α-aminodicarboxylic acids can be used as well. Both of them can be reacted with an alkali sulfite or alkali bisulfite to yield the end-products of the general formula (I).

According to process variants (g) and (h) of the invention, an ω-amide of an α-substituted dicarboxylic acid, wherein the substituent in the α-position is other than amino, is reacted to introduce an amino group into the α-position. As starting substances, e.g. the α-nitro-, α-arylazo-, α-hydrazo-, α-arylhydrazo-, α-hydroxylamino-, α-oxyimino- or α-iminodicarboxylic acid-ω-amides or the ω-amides of the α-ketodicarboxylic acid hydrazones can be used. Starting from these compounds, the end-products of the general formula (I) can be obtained by reduction, preferably by catalytic hydrogenation. If the ω-amide of an α-halo- or α-p-toluenesulfonyloxy-dicarboxylic acid is used as starting substance, the aimed α-amino compounds can be obtained by reacting the starting substances with ammonia. Various methods can be utilized to convert α-keto-dicarboxylic acid-ω-amides into α-amino-dicarboxylic acid amides. The keto group can be converted into amino group e.g. by reacting the keto compound with potassium cyanide in the presence of ammonium hydroxide, and hydrogenating the obtained intermediate in the presence of cobalt chloride (Bull. Chem. Soc. Japan 36, 763 /1963/). If the α-ketocarboxylic acid derivative is condensed with optically active α-methyl-benzylamine, and the intermediate is hydrogenated, the aimed α-amino compound is obtained in optically active form (J. Am. Chem. Soc. 83, 4798 /1961/).

Process variant (i) of the invention proceeds via an intermediate prepared by a malonester synthesis. The removal of the ester groups and the partial decarboxylation can be performed in a single step by admixing the intermediate with 48% hydrobromic acid and allowing the mixture to stand for one day or heating it gently for several hours.

If a compound containing a halogen atom or a double bond in the side chain of the α-aminodicarboxylic acid moiety is used as starting substance or intermediate, the compounds of the general formula (I) can be prepared by hydrogenation (see process variant j/ of the invention). One can also use such compounds that contain a halogen atom or a double bond in the side chain of an α-substituted dicarboxylic acid moiety which can be converted by hydrogenation into α-aminodicarboxylic acid (see process variants g/ and h/ of the invention).

According to process variant (k) of the invention an α-amino-glutarimide or α-amino-succinimide is converted first into its alkali metal salt, and subsequently the imino nitrogen is alkylated. As alkylating agent e.g. 2-bromo-ethanesulfonic acid or 3-bromo-propanesulfonic acid can be used. The obtained N-sulfoethyl or N-sulfopropyl derivative is then subjected to partial hydrolysis in a slightly alkaline medium. In this reaction the cyclic intermediate converts primarily into the respective ω-amide, which can be separated from the small amount of α-amide by ion exchange chromatography.

Process variant (l) of the invention also leads to compounds of the general formula (I). When reacting 5-carboxypyrrolid-1-one ("pyroglutaminic acid") or 6-carboxy-piperid-1-one e.g. with taurine, homotaurine, N-methyl-taurine etc., or with another amine containing a strongly acidic functional group, or with an alkali metal or tertiary base salt of these compounds, the lactam ring splits and ω-amides are formed.

According to process variant (m) of the invention, the ω-amides are prepared via azlactone type intermediates. The saturation of the double bond of the molecule and the removal of the oxazolone ring can be performed by hydrogenation and subsequent partial hydrolysis. As another method, the compound can be heated in a glacial acetic acid medium in the presence of red phosphorous and hydrogen iodide.

The substituted derivatives of the compounds having the general formula (I) can be prepared by various methods. One of these methods is to remove one of the protecting groups of an intermediate containing protecting groups on both the α-amino and the α-carboxy groups. According to process variant (p) of the invention, only the amino-protecting group is removed. In this case one must apply a selective method. Thus, for example, a mixture of glacial acetic acid and hydrobromic acid can be used to advantage for N-carbobenzyloxy-α-benzyl ester derivatives. Process variant (r) of the invention is particularly suitable for the selective splitting of the α-ester group, e.g. by alkaline saponification.

Partially substituted derivatives can also be prepared from the compounds of the general formula (I) containing free amino and free α-carboxy groups. Process variant (s) of the invention yields acyl derivatives, whereas process variant (t) of the invention yields the esterified analogues by simple, well-known methods. Thus, for example, acetyl, benzoyl or p-toluenesulfonyl derivatives can be prepared, or the compounds containing free carboxy groups can be esterified, preferably in the presence of gaseous hydrochloric acid, with an alcohol to obtain e.g. $C_{1-4}$ alkyl esters, aryl esters, aralkyl esters, etc.

According to process variant (x) of the invention a peptide containing an α-amino-dicarboxylic acid moiety (e.g. α-glutamyl-glycine) is activated on its ω-carboxy group (e.g. converted into its p-nitrophenyl ester), and this compound is used to acylate taurine, homotaurine or cholamine phosphate.

Finally, the oligomeric or polymeric derivatives of the compounds having the general formula (I) can also be prepared according to the invention. Thus, according to process variant (u), an α-poly-aminodicarboxylic acid-ω-(activated) ester, such as α-poly-L-glutaminic acid-ω-p-nitrophenyl ester is reacted with taurine, homotaurine or cysteamine to obtain the desired compounds (when using cysteamine an oxydation step should also be inserted). If desired, these polymers can be decomposed into the monomeric substances of the general formula (I) using the method of process variant (v). The decomposition can be performed by enzymatic hydrolysis using e.g. carboxypeptides or leucinaminopeptidase.

The invention is elucidated in detail by the aid of the following non-limiting Examples.

EXAMPLE 1

40.85 g. (0.11 moles) of carbobenzyloxy-L-glutaminic acid-α-benzyl ester (Liebig's Ann. 655, 200 /1962/) are dissolved in 500 ml. of acetonitrile. The solution is cooled to −15° C. under exclusion of air humidity, and 15.4 ml. (0.11 moles) of triethylamine are added to the stirred mixture followed by 15.4 ml. (0.11 moles) of isobutyl chloroformate. The mixture is stirred at −15° C. for 40 minutes, thereafter 28 ml. (0.2 moles) of triethylamine, 11.26 g. (0.05 moles) of cystamine dihydrochloride, and finally 250 ml. of acetonitrile are added. The mixture is stirred vigorously at −15° C. for 2 hours and then at room temperature for 4 hours.

The reaction mixture is evaporated in vacuo at 30° C. The residue is admixed with 200 ml. of ice-cold water under cooling and stirring, and the obtained mixture is evaporated in vacuo at 35° C. 250 ml. of water and 500 ml. of ethyl acetate are added to the residue, and the mixture is poured into a separation funnel. The ethyl acetate phase is washed successively with 250 ml. of water, 2×250 ml. of 5% aqueous sodium carbonate solution, 2×250 ml. of 1 n hydrochloric acid and 250 ml. of water. (The aqueous-alkaline wash can be acidified with hydrochloric acid and extracted with ether to obtain about 5 g. of non-reacted carbobenzyloxy-L-glutaminic acid-α-benzyl ester.) The ethyl acetate solution is dried over anhydrous sodium sulfate, and evaporated to dryness in vacuo at 30° C. A thick, oily residue is obtained which crystallizes upon standing. The residue is triturated with 250 ml. of absolute ether, the crystalline substance is filtered off, and the thus-obtained crude product, weighing about 40 to 42 g., is recrystallized from 100 ml. of ethyl acetate and 170 ml. of ether. 29.3 g. of N,N'-bis-(N-carbobenzyloxy-gamma-/α-benzyl/-L-glutamyl)-cystamine are obtained: m.p.: 91°–92° C.

Analysis: Calculated for $C_{44}H_{50}N_4O_{10}S_2$ (M=859.05): C: 61.52% H: 5.89% N: 6.52% S: 7.46%. Found: C: 60.85% H: 5.91% N: 6.61% S: 7.72%.

EXAMPLE 2

25.77 g. (0.03 moles) of N,N'-bis-(N-carbobenzyloxygamme-/α-benzyl/-L-glutamyl)-cystamine (prepared as described in Example 1) are dissolved in 75 ml. of glacial acetic acid. The solution is cooled in an ice bath and a freshly prepared mixture of 75 ml. 30% hydrogen peroxide and 225 ml. of glacial acetic acid is added dropwise within 15 minutes. Thereafter the ice bath is removed, the mixture is stirred at room temperature for 4 hours, and evaporated in vacuo at 30° C. the oily product is dried in a desiccator first over phosphorous pentoxide and then over solid potassium hydroxide. 28.5 g. of carbobenzyloxy-gamma-(α-benzyl)-L-glutamyltaurine are obtained. This crude product can be used without purification in the preparation of gamma-L-glutamyl-taurine.

EXAMPLE 3

26.32 g. (55 mmoles) of carbobenzyloxy-gamma-(α-benzyl)-L-glutamyl-taurine (prepared as described in Example 2) are dissolved in 50 ml. of glacial acetic acid, and 50 ml. of glacial acetic acid containing 4 moles of hydrogen bromide are added. A vigorous carbon dioxide development sets in. The mixture is allowed to stand at room temperature for 2 hours, and then evaporated in vacuo at 30° C. The oily residue is dissolved in 170 ml. of water, and the solution is washed with 5×70 ml. of ether. The aqueous phase is evaporated in vacuo at 35° C. 20.42 g. of gamma-(α-benzyl)-L-glutamyltaurine are obtained. The product can be recrystallized from 90% aqueous ethanol. $R_f$=0.53 (in a 15:10:3:12 mixture of n-butanol, pyridine, glacial acetic acid and water); 0.39 (in a 4:1:1 mixture of n-butanol, glacial acetic acid and water).

EXAMPLE 4

529 mg. (1.1 mmoles) of carbobenzyloxy-gamma-(α-benzyl)-L-glutamyl-taurine (prepared as described in Example 2) are dissolved in 5 ml. of 1 N aqueous potassium hydroxide solution, and the mixture is allowed to stand at room temperature for 4 hours. The solution is washed with 3×3 ml. of ether, passed through a 1 cm.×20 cm. column filled with Dowex 50×2 resin, and the column is eluted with water. 50 ml. of eluate are collected and evaporated to dryness in vacuo at 35° C. The obtained crude carbobenzyloxy-gamma-L-glutamyl-taurine is purified by paper electrophoresis at pH 6.5. Relative motility (related to cysteinic acid): 1.05. $R_f=0.57$ (in a 15:10:3:12 mixture of n-butanol, pyridine, glacial acetic acid and water).

EXAMPLE 5

5.79 g. (12.1 mmoles) of carbobenzyloxy-gamma-(α-benzyl)-L-glutamyl-taurine (prepared as described in Example 2) are dissolved in a mixture of 100 ml. of ethanol and 25 ml. of water. 0.5 g. of 10% palladium-on-carbon catalyst are added, and the mixture is hydrogenated under shaking. It is advantageous to add two further portions of the catalyst (0.25 g. each) to the mixture during the reaction. When the hydrogen uptake ceases the catalyst is filtered off, the filtrate is evaporated in vacuo at 30° C., and the oily residue is dried in a desiccator over phosphorous pentoxide, 3.1 g. of gamma-L-glutamyl-taurine are obtained. The product is highly water-soluble, but is insoluble in alcohol. It can be crystallized by dissolving it in a minimum amount of water and adding to the solution in small portions. The crude crystalline substance melts at 202°–204° C.

The product is recrystallized several times from 80% ethanol, 2.02 g. (66%, calculated for the starting N,N'-bis-/N-carbobenzyloxy-gamma-(α-benzyl)-L-glutamyl/-cystamine) of the purified product are obtained; m.p.: 219°–220° C.: $(\alpha)_D^{20}=+14°$ (water, c=1.02).

Relative motility values in paper electrophoresis (related to cysteinic acid): 0.73 at pH 6.5, and 0.53 at pH 1.8. $R_f=0.19$ (in a 15:10:3:12 mixture of n-butanol,pyridine, glacial acetic acid and water).

Analysis: Calculated for $C_7H_{14}N_2O_6S$ (M=254.27): C: 33.07% H: 5.55% N: 11.02% O: 37.75% S: 12.61%. Found: C: 33.15% H: 5.76% N: 10.94% O: 37.53% S: 12.17%.

EXAMPLE 6

20.42 g. of gamma-(α-benzyl)-L-glutamyl-taurine (prepared as described in Example 3) are dissolved in 150 ml. of 1 N aqueous potassium hydroxide solution. The mixture is allowed to stand at room temperature for 4 hours, then it is poured onto a 2 cm.×100 cm. column filled with Dowex 50×2 resin (Fluke, 100–200 mesh, H+ cycle), and the column is eluted with water. 300 ml. of eluate are collected from the start of the washing step, and this eluate is evaporated in vacuo at 35° C. The oily residue is crystallized by adding 8–10 ml. of water and about 100 ml. of ethanol. The crystals are filtered off, washed with alcohol, and dried. 13.7 g. of gamma-L-glutamyl-taurine are obtained. The product is recrystallized from 80% aqueous ethanol. 9.79 g. (70%, calculated for N,N'-bis-(N-carbobenzyloxy-gamma-/α-benzyl/-L-glutamyl)-cystamine) of the purified product are obtained.

EXAMPLE 7

5.42 g. (11 mmoles) of carbobenzyloxy-L-glutaminic acid-(α-benzyl)-gamma-p-nitrophenylester (Chem. Ber. 96, 204/1963/) are dissolved in 50 ml. of pyridine. The solution is cooled to 0° C., and a solution in 1.25 g. (10 mmoles) of taurine in 20 ml. of water is added dropwise within 30 minutes under vigorous stirring. Thereafter 3.08 ml. (22 mmoles) of triethylamine are added dropwise to the mixture, and cooling and stirring are discontinued. The mixture is left to stand at room temperature for 72 hours and then evaporated in vacuo. The residue is dissolved in 50 ml. of water, and 1 n hydrochloric acid is added to the solution until the disappearance of the yellow colour. The solution is washed with 10×50 ml. of ether in order to remove p-nitrophenol, and the aqueous phase is evaporated in vacuo. 6.9 g. of carbobenzyloxygamma-(α-benzyl)-L-glutamyl-taurine triethylammonium salt are obtained.

This compound is subjected to catalytic hydrogenation as described in Example 5, thereafter the solvent is evaporated in vacuo, the residue is dissolved in a minimum amount of water, and the solution is poured onto a 2×40 cm. column filled with Dowex 50×2 resin. The resin column is eluted with water. About 120 ml. of eluate are collected and evaporated in vacuo at 35° C. The residue is crystallized and the product is purified as described in Example 5. 1.72 g. (68%, calculated for taurine) of gamma-L-glutamyltaurine are obtained.

EXAMPLE 8

Carbobenzyloxy-gamma-L-glutamyl-taurine, obtained as described in Example 4, is dissolved in 2 ml. of glacial acetic acid containing 4 moles of hydrogen bromide. The mixture is allowed to stand at room temperature for 30 minutes, and then evaporated in vacuo at 35° C. The residue is triturated several times with ether; the etheral solutions are decanted. The substance is recrystallized as described in Example 5, to yield gamma-L-glutamyl-taurine.

EXAMPLE 9

10 ml. of a 0.01 N aqueous sodium hydroxide solution are added to the solution of 25.4 mg. (0.1 mmoles) of gamma-L-glutamyl-taurine in 2 ml. of water, and the mixture is evaporated to dryness in vacuo at 35° C. The white, crystalline residue is dried in a desiccator over phosphorous pentoxide. The mono-sodium salt of gamma-L-glutamyl-taurine is obtained. The product is spairingly soluble both in methanol and ethanol. The product has no sharp melting point; it starts to shrink at about 200° C., and carbonizes at about 250° C.

EXAMPLE 10

10 ml. of absolute methanol, containing 0.5 moles/l. of hydrogen chloride, are added to 7.5 mg. (30 micromoles) of gamma-L-glutamyl-taurine, and the suspension is stirred at room temperature for 24 hours. The product is isolated in pure state by descending paper chromatography. $R_f=0.27$ (in a 15:10:3:12 mixture of n-butanol, pyridine, glacial acetic acid and water) and 0.14 (in a 4:1:1 mixture of n-butanol, glacial acetic acid and water).

EXAMPLE 11

One proceeds as described in Example 10 with the difference that ethanol is substituted for methanol. This way the corresponding ethyl ester, i.e. gamma-(α-ethyl)-L-glutamyl-taurine is obtained. $R_f=0.37$ (in a 15:10:3:12 mixture of n-butanol, pyridine, glacial acetic acid and water) and 0.22 (in a 4:1:1 mixture of n-butanol, glacial acetic acid and water).

EXAMPLE 12

25.4 mg. (0.1 mmoles) of gamma-L-glutamyl-taurine are dissolved in 100 μl. of 2 N aqueous sodium hydroxide solution, and a total amount of 36 μl. of acetic anhydride and 180 μl. of 4 N aqueous sodium hydroxide solution are added to the vigorously stirred mixture in three portions. The mixture is stirred for 5 minutes each after the addition of the individual portions. Finally the alkaline solution is diluted with water to 2 ml., and allowed to stand at room temperature for 12 hours. Thereafter the solution is poured onto a 1 cm.×10 cm. column filled with Dowex 50×2 resin, and the column is eluted with water. 50 ml. of eluate are collected, and this solution is evaporated in vacuo at 35° C. The obtained N-acetyl-gamma-L-glutamyl-taurine is dissolved in water and purified by paper electrophoresis using a pH 6.5 buffer. Relative motility (related to cysteinic acid): 1.22. $R_f=0.25$ (in a 15:10:3:12 mixture of n-butanol, pyridine, glacial acetic acid and water).

EXAMPLE 13

25.4 mg. (0.1 mmoles) of gamma-L-glutamyl-taurine are treated with 13 μl. of benzoyl chloride as described in Example 12. The reaction mixture is processed as described in Example 12 to obtain N-benzoyl-gamma-L-glutamyl-taurine, which is purified by paper electrophoresis using a pH 6.5 buffer solution. Relative motility (related to cysteinic acid): 1.06. $R_f=0.47$ (in a 15:10:3:12 mixture of n-butanol, pyridine, glacial acetic acid and water).

EXAMPLE 14

0.48 g. (1 millimole) of carbobenzyloxy-α-L-glutamyl-(gamma-p-nitrophenylester)-glycine ethyl ester (Acta Chim. Acad. Sci. Hung. 65, 375 /1970/) are dissolved in 6 ml. of ethyl acetate. The solution is cooled with ice water to 0° C., and a solution of 0.08 g. (1 mmole) of cysteamine in 1 ml. of dimethyl formamide is added. Thereafter 0.14 ml. (1 mmole) of triethylamine are added dropwise to the solution. A precipitate starts slowly to separate. The reaction mixture is allowed to stand in ice water and then at room temperature for one day. The mixture is diluted with a 1:1 mixture of ethyl acetate and ether, the precipitate is separated by centrifuging, and washed several times with a 4:1 mixture of ether and ethyl acetate and finally with ether. The precipitate is dried over sulfuric acid, then washed successively thrice with 1 N hydrochloric acid, twice with water, twice with saturated sodium hydrocarbonate solution and again twice with water, and dried in vacuo over sulfuric acid. 0.35 g. (85%) of carbobenzyloxy-α-L-glutamyl-(gamma-cysteamine)-glycine ethyl ester are obtained.

Analysis: Calculated for $C_{18}H_{25}O_6N_3S$ (M=411.4): C: 52.6% H: 6.1% S: 7.8%. Found: C: 53.4% H: 6.5% S: 7.7%.

IR-spectrum: characteristic maxima at 3310 (NH), 1748 (ester carbonyl), 1690 (C=O /carbobenzyloxy/) and 1655 (amide carbonyl) $cm^{-1}$.

100 mg. of carbobenzyloxy-α-L-glutamyl-(gamma-cysteamine)-glycine ethyl ester are dissolved in 2 ml. of glacial acetic acid, and 0.5 ml. of 30% hydrogen peroxide are added to the solution. The reaction mixture is allowed to stand in an ice bath for 4 hours. The progress of the reaction is monitored by electrophoresis. When the raction terminates the mixture is diluted with water and subjected to freeze drying. 0.11 g. of solid, foam-like carbobenzyloxy-α-L-glutamyl-(gamma-taurine)-glycine ethyl ester are obtained; yield: 95%.

EXAMPLE 15

0.47 g. (1 mmole) of carbobenzyloxy-α-L-glutamyl-(gamma-p-nitrophenylester)-glycine methyl ester are dissolved in 6 ml. of pyridine. The solution is cooled in an ice bath and a solution of 0.125 g. (1 mmole) of taurine in 2 ml. of water is added, followed by 0.28 ml. (2 mmoles) of triethylamine. The reactants should be added in small portions so as to obtain always a clear solution. The reaction mixture is allowed to stand at room temperature for three days and then evaporated in vacuo. The oily residue is triturated with ether and petroleum ether and dried in vacuo over sulfuric acid. Carbobenzyloxy-α-L-glutamyl-(gamma-taurine)-glycine methyl ester is obtained.

EXAMPLE 16

100 mg. of carbobenzyloxy-α-L-glutamyl-(gamma-taurine)-glycine ethyl ester (prepared as described in Example 14) are dissolved in a mixture of 1 ml. of trifluoroacetic acid and 1 ml. of concentrated hydrochloric acid. The solution is maintained at 35° C. for three hours in a sealed tube. The obtained solution is evaporated in vacuo, the residue is triturated several times with ether and n-hexane, and finally evaporated again. 0.06 g. (88%) of α-L-glutamyl-(gamma-taurine)-glycine are obtained as a white, amorphous substance. On the basis of electrophoresis the product is uniform and gives a positive ninhydrine reaction.

Analysis: Calculated for $C_9H_{17}N_3O_7S$ (M=311.3): S: 10.3%. Found: S: 10.0%.

IR-spectrum: characteristic bands appear at 3100 (broad, $NH_3^+$), 3200 (broad, carboxy OH), 1730 (carboxy carbonyl), 1680 (amide carbonyl), 1560 (amide carbonyl), 1220 (intense, sulfonic acid S=O) and 1045 (intense, sulfonate S=O) $cm^{-1}$.

20 mg. of the above substance are admixed with 1 ml. of 6 N hydrochloric acid, and the mixture is heated at 105° C. for 24 hours in a sealed tube. After cooling, a sample of the solution is subjected to electrophoresis. The sample contains glutaminic acid, glycine and taurine.

EXAMPLE 17

100 mg. of carbobenzyloxy-α-L-glutamyl-(gamma-taurine)-glycine methyl ester (prepared as described in Example 15) are treated with 4 ml. of 2 N hydrobromic acid in glacial acetic acid at room temperature until complete dissolution takes place (for about 30 minutes). The obtained clear solution is poured into 30 ml. of ether, and the mixture is allowed to stand at a cold place for one day. The separated substance is removed by centrifuging, washed several times with ether, and dried in vacuo over potassium hydroxide, sulfuric acid and phosphorous pentoxide, α-L-glutamyl-(gamma-taurine)-glycine methyl ester hydrobromide salt is obtained. On the basis of electrophoresis the obtained product is practically completely pure.

EXAMPLE 18

The salt obtained according to Example 17 is treated with 2 ml. of 1 N sodium hydroxide solution for 3 hours under ice cooling. The progress of the hydrolysis is monitored by electrophoresis. The reaction mixture is treated with 10 ml. of Dowex 50 ion exchanger ($H^+$ form) and freeze-dried. On the basis of electrophoresis, the obtained substance still contains impurities. The crude product is recrystallized several times from aqueous ethanol, until the required purity is attained. 40 mg. (59%) of α-L-glutamyl-(gamma-taurine)-glycine are obtained.

IR-spectrum: characteristic bands appear at 3310 (NH), 3100 (broad, $NH_3^+$), 1730 (carboxy carbonyl), 1650 (amide carbonyl), 1570 (amide carbonyl), 1220 (intense, S=O), and 1045 (intense) $cm^{-1}$.

EXAMPLE 19

100 mg. of α-L-glutamyl-(gamma-taurine)-glycine (prepared as described in Example 16 or 18) are dissolved in 25 ml. of 0.2 molar ammonium hydrocarbonate buffer (pH=8.5), and a solution of 1 mg. of carboxypeptidase-A (Serva, Heidelberg) in 0.5 ml. of water is added. The mixture is thermostated at 37° C. for 24 hours, and then freeze-dried. The dry residue contains gamma-L-glutamyl-taurine and glycine. From this mixture gamma-L-glutamyl-taurine can be separated in pure state by electrophoresis or by chromatography using Dowex 50 ion exchanger.

EXAMPLE 20

0.52 g. (4 mval.) of α-poly-L-glutaminic acid with a polymerization grade of 80 (Acta Chim. Acad. Sci. Hung. 5, 267 /1955/) are dissolved in 10 ml. of dimethyl formamide, and 1.39 g. (10 mmoles) of p-nitrophenol and 0.82 g. (4 mmoles) of dicyclohexyl carbodiimide are added to the solution under stirring and ice cooling. After 10 minutes the dicyclohexyl urea starts to separate. The mixture is stirred at room temperature for one day, and the separated dicyclohexyl urea is filtered off. 0.3 ml. of glacial acetic acid are added to the filtrate to convert the non-reacted dicyclohexyl carbodiimide into dicyclohexyl urea, and the separated substance is filtered off. The filtrate is poured into a mixture of 100 ml. of ether, 100 ml. of petroleum ether, 20 ml. of ethyl acetate and 2 ml. of glacial acetic acid. The separated substance is isolated by centrifuging, washed several times with ether, and dried in vacuo over sulfuric acid. 0.80 g. of α-poly-L-glutaminic acid-p-nitrophenylester-1 are obtained, containing 2.6 mval./g. of p-nitrophenolate.

IR-spectrum: characteristic bands appear at 3300 (NH), 1765 (COONP carbonyl), 1660 (amide carbonyl), 1550 (amide carbonyl), 1530 ($NO_2$) and 1360 ($NO_2$) $cm^{-1}$.

0.25 g. of the above compound are dissolved in 7 ml. of pyridine, and a solution of 0.125 g. (1 mmole) of taurine in 1 ml. of water and 0.28 ml. (2 mmoles) of triethylamine is added in ten portions to the stirred mixture. The reactant is added at a rate to obtain always a clear solution. 1 ml. of water is added to the mixture, and the mixture is maintained at room temperature for 3 days. The solution is evaporated in vacuo, the residue is dried, and triturated well with ether. The obtained powdery substance is dissolved in water and the solution is freeze-dried. 0.20 g. of α-poly-gamma-L-glutamyl-taurine-1 are obtained. On the basis of chromatographical examination the product contains 0.4% of taurine contamination.

Analysis: S: 10.1%

IR-spectrum: characteristic bands appear at 3100-3400 (broad, OH), 1650 (amide carbonyl), 1550 (amide carbonyl), 1220, 1040 and 600 (sulfonic acid S=O) $cm^{-1}$.

EXAMPLE 21

0.26 g. (2 mval.) of α-poly-L-glutaminic acid with a polymerization grade of 580 (J. Am. Chem. Soc. 80, 4631 /1958/) are swollen and dissolved in 15 ml. of dimethyl formamide, and 0.69 g. (5 mmoles) of p-nitrophenol and 0.41 g. (2 mmoles) of dicyclohexyl carbodiimide are added to the stirred solution. The reaction mixture is stirred for 2 days at room temperature. 0.30 g. of α-poly-L-glutaminic acid-p-nitrophenyl ester-2 are obtained.

IR-spectrum: the spectrum is similar to that discussed in Example 20 but the bands are broader and also an acid carbonyl band appears at 1720 $cm^{-1}$.

The above compound is reacted as described in Example 20 to obtain 270 mg. of freeze-dried α-poly-gamma-L-glutamyl-taurine-2. On the basis of chromatographical examination the product contains less than 0.4% of taurine impurity.

Analysis: S: 7.3%.

IR-spectrum: identical with the above.

EXAMPLE 22

0.26 g. (2 mval.) of α-L-polyglutaminic acid with a polymerization grade of 580 are dissolved in 8 ml. of dimethyl formamide, and the solution is cooled to −10° C. in a salted ice bath. Upon the addition of 0.28 ml. (2 mmoles) of triethylamine a gel is formed, which cannot be dissolved even when adding further 8 ml. of dimethyl formamide and applying vigorous stirring. 0.28 ml. (2 mmoles) of isobutyl chloroformate are added dropwise to the mass, and after 30 minutes of activation a solution of 0.16 g. (2 mmoles) of cysteamine in 2 ml. of dimethyl formamide is added dropwise. The mixture is stirred at −5° C. for 2 hours and then at room temperature for 4 hours, finally it is poured into a mixture of 50 ml. of chloroform and 50 ml. of petroleum ether. The separated white precipitate is isolated by centrifuging, washed several times with petroleum ether containing chloroform, swollen several times with alcohol, and finally precipitated with ether. 0.33 g. of α-poly-gamma-L-glutamylcysteamine are obtained.

Analysis: S: 14.7%.

0.16 g. of α-poly-gamma-L-glutamyl-cysteamine are suspended in 5 ml. of glacial acetic acid, and 1 ml. of 30% hydrogen peroxide is added. The reaction mixture is allowed to stand at room temperature for 3 days. A clear solution is obtained slowly. The solution is diluted with water, filtered, and the filtrate is freeze-dried. 0.20 g. of white α-poly-gamma-L-glutamyl-taurine are obtained. On the basis of chromatographical examination the product contains 0.5% of taurine impurity.

Analysis: S: 11.9%.

IR-spectrum: identical with those described above.

EXAMPLE 23

1.083 g. (2.2 mmoles) of carbobenzyloxy-L-glutaminic acid-(α-benzyl)-gamma-nitrophenyl ester are dissolved in 6 ml. of a 2:1 mixture of pyridine and water, and 278 mg. (2 mmoles) of homotaurine and 0.59 ml. (4.2 mmoles) of triethylamine are added to the solution. The yellow solution is allowed to stand at room temperature for 72 hours, and then it is evaporated in vacuo. The oily residue is dissolved in water, neutralized with hydrochloric acid, and extracted with ether in an extractor of continuous operation for 8 hours in order to remove p-nitrophenol. The aqueous phase is evaporated in vacuo. 1.68 g. of carbobenzyloxy-gamma-($\alpha$-benzyl)-L-glutamyl-homotaurine are obtained.

EXAMPLE 24

The total amount of the product obtained in Example 23 is dissolved in 10 ml. of 50% aqueous ethanol, 0.3 g. of 10% palladium-on-carbon catalyst are added, and gaseous hydrogen is bubbled through the suspension for 4 hours. Thereafter the catalyst is filtered off and the filtrate is evaporated in vacuo. The residue is dissolved in 1-2 ml. of water, passed through a 1 cm.$\times$35 cm. column filled with Dowex 50$\times$2 resin (H$^+$ cycle), and the column is eluted with water. 50 ml. of eluate are collected, and this solution is evaporated in vacuo. 440 mg. (82%) of gamma-L-glutamyl-homotaurine are obtained as residue. On the basis of paper electrophoresis performed at pH 6.5 the crude product contains a small amount of neutral and acidic contaminations (homotaurine and glutaminic acid). The crude product can be purified e.g. by preparative electrophoresis.

In paper electrophoresis performed at pH 6.5 and 1.8, respectively, the substance always migrates towards the cathode. Relative motility values (related to cysteinic acid): 0.68 and 0.50, respectively, $R_f=0.19$ (in a 15:10:3:12 mixture of n-butanol, pyridine, glacial acetic acid and water).

EXAMPLE 25

1.083 g. (2.2 mmoles) of carbobenzyloxy-L-glutaminic acid-($\alpha$-benzyl)-gamma-p-nitrophenyl ester are reacted with 278 mg. (2 mmoles) of N-methyl-taurine as described in Example 23. 1.59 g. of carbobenzyloxy-gamma-($\alpha$-benzyl)-L-glutamyl-N-methyl-taurine are obtained.

EXAMPLE 26

1.59 g. of the product obtained according to Example 25 are subjected to catalytic hydrogenation as described in Example 24. 423 mg. (79%) of gamma-L-glutamyl-N-methyl-taurine are obtained.

In paper electrophoresis performed at pH 6.5 and 1.8, respectively, the substance always migrates towards the cathode. Relative motility values (related to cysteinic acid): 0.68 and 0.49, respectively. $R_f=0.16$ (in a 15:10:3:12 mixture of n-butanol, pyridine, glacial acetic acid and water).

EXAMPLE 27

2.87 g. (6.6 mmoles) of carbobenzyloxy-L-glutaminic acid-($\alpha$-benzyl)-gamma-p-nitrophenyl ester are dissolved in 20 ml. of pyridine, and a solution of 1.25 g. (6 mmoles) of L-cysteinic acid monohydrate in a mixture of 17 ml. of water and 17 ml. of pyridine is added. 2.6 ml. (18.6 mmoles) of triethylamine are added to the mixture, and the reaction mixture is allowed to stand at room temperature for 72 hours. The solution is evaporated in vacuo at 30° C. The residue is dissolved in 20 ml. of water, the solution is acidified with concentrated hydrochloric acid, and washed with 15$\times$10 ml. of ether. The aqueous phase is evaporated in vacuo at 35° C. Carbobenzyloxy-gamma-($\alpha$-benzyl)-L-glutamyl-L-cysteinic acid are obtained.

EXAMPLE 28

The product obtained according to Example 27 is dissolved in 20 ml. of water, 0.3 g. of 10% palladium-on-carbon catalyst are added, and hydrogen is bubbled through the suspension for 3 hours. The reaction mixture is processed as described in Example 24 to obtain gamma-L-glutamyl-L-cysteinic acid; m.p.: 187° C. Relative motility values in paper electrophoresis (related to cysteinic acid): 1.21 at pH 6.5, and 0.54 at pH 1.8.

EXAMPLE 29

1.083 g. (2.2 mmoles) of carbobenzyloxy-L-glutaminic acid-($\alpha$-benzyl)-gamma-p-nitrophenyl ester are dissolved in 6 ml. of a 2:1 mixture of pyridine and water, and 282 mg. (2 mmoles) of cholamine phosphate (U.S. Pat. No. 2,730,542) and 0.87 ml. (6.2 mmoles) of triethylamine are added to the solution. The mixture is allowed to stand at room temperature for 72 hours and then it is evaporated in vacuo. The residue is processed as described in Example 23. 1.25 g. of carbobenzyloxy-gamma-($\alpha$-benzyl)-L-glutamyl-cholamine phosphate are obtained.

EXAMPLE 30

1.25 g. of the product obtained according to Example 29 are subjected to catalytic hydrogenation in order to remove the protecting group. The hydrogenation and the processing of the reaction mixture are identical with those described in Example 24. 470 mg. (91%) of gamma-L-glutamyl-cholamine phosphate are obtained. On the basis of paper electrophoresis this substance contains about 15 to 20% of cholamine phosphate as impurity. The crude product can be purified e.g. by electrophoresis.

In paper electrophoresis performed at pH 6.5 and 1.8, respectively, the substance always migrates towards the cathode. Relative motility values (related to cysteinic acid): 0.75 and 0.36, respectively. $R_f=0.18$ (in a 15:10:3:12 mixture of n-butanol, pyridine, glacial acetic acid and water).

EXAMPLE 31

526 mg. (1.1 mmoles) of carbobenzyloxy-L-aspartic acid-($\alpha$-benzyl)-$\beta$-p-nitrophenyl ester (Chem. Ber. 97, 1789 /1964/) are dissolved in 5 ml. of pyridine. The solution is cooled to 0° C., and a solution of 125 mg. (1 mmole) of taurine in 2 ml. of water is added in small portions followed with 0.28 ml. (2 mmoles) of triethylamine. The reaction mixture is allowed to stand at room temperature for 48 hours, and then evaporated in vacuo. The residue is dissolved in 5 ml. of water, and 1 N hydrochloric acid is added dropwise to the solution until the disappearance of the yellow colour. The solution is washed with 10$\times$5 ml. of ether in order to remove p-nitrophenol. The aqueous phase is evaporated in vacuo. 478 mg. of carbobenzyloxy-$\beta$-($\alpha$-benzyl)-L-aspartyl-taurine are obtained.

EXAMPLE 32

The total amount of the product obtained according to Example 31 is dissolved in 6 ml. of 50% aqueous ethanol, 100 mg. of 10% palladium-on-carbon catalyst are added, and hydrogen is bubbled through the suspension for 4 hours. The catalyst is filtered off, the filtrate is evaporated in vacuo, and the triethylamine is removed from the residue as described in Example 24. 172 mg. (71%) of β-L-aspartyl-taurine are obtained. The product contains a small amount of taurine as impurity, which can be removed e.g. by electrophoresis.

In paper electrophoresis performed at pH 6.5 and 1.8, respectively, the substance always migrates towards the cathode. Relative motility values (related to cysteinic acid): 0.77 and 0.58, respectively. $R_f=0.16$ (in a 15:10:3:12 mixture of n-butanol, pyridine, glacial acetic acid and water).

EXAMPLE 33

526 mg. (1.1 mmoles) of carbobenzyloxy-L-aspartic acid-(α-benzyl)-β-p-nitrophenyl ester are reacted with 139 mg. (1 mmole) of homotaurine as described in Example 31 to yield carbobenzyloxy-β-(α-benzyl)-L-aspartyl-homotaurine.

EXAMPLE 34

The product of Example 33 is subjected to catalytic hydrogenation as described in Example 24. 203 mg. of β-L-aspartyl-homotaurine are obtained; yield: 84%.

In paper electrophoresis performed at pH 6.5 and 1.8, respectively, the substance always migrates towards the cathode. Relative motility values (related to cysteinic acid): 0.72 and 0.53, respectively. $R_f=0.17$ (in a 15:10:3:12 mixture of n-butanol, pyridine, glacial acetic acid and water).

EXAMPLE 35

Carbobenzyloxy-L-aspartic acid-(α-benzyl)-β-p-nitrophenyl ester is reacted with cholamine phosphate as described in Example 29 to obtain carbobenzyloxy-β-(α-benzyl)-L-aspartyl-cholamine phosphate.

EXAMPLE 36

The substance obtained in Example 35 is subjected to catalytic hydrogenation as described in Example 24 to obtain β-L-aspartyl-cholamine phosphate.

In paper electrophoresis performed at pH 6.5 and 1.8, respectively, the substance always migrates towards the cathode. Relative motility values (related to cysteinic acid): 0.81 and 0.40, respectively. $R_f=0.14$ (in a 15:10:3:12 mixture of n-butanol, pyridine, glacial acetic acid and water).

EXAMPLE 37

Crude gamma-L-glutamyl-taurine obtained according to Example 5, 6, 7, 8 or 19 can be purified by recrystallization as follows: 300 mg. of the crude substance are dissolved at room temperature with stirring in 5 ml. of dry dimethyl sulfoxide. The opale solution is filtered, and the filter is washed with 0.5 ml. of dry dimethyl sulfoxide. The filtrate is combined with the wash, and 55 ml. of absolute ethanol are added. The mixture is allowed to stand at room temperature for 12 hours. The separated substance is filtered off, washed with 2.5 ml. of absolute ethanol, and dried in a vacuum desiccator over phosphorous pentoxide until constant weight. 240 mg. of crystalline gamma-L-glutamyl-taurine are obtained (recovery: 80%).

In the above procedure ethanol can be replaced by an equal amount of dry dioxane, ether or acetone. The quality of the crystalline product is always the same. M.p. (Boetius): 218°–219° C. On the basis of layer chromatography the product is uniform.

EXAMPLE 38

Carbobenzyloxy-gamma-(α-benzyl)-L-glutamyl-cholamine is prepared by the method generally applicable for the preparation of glutaminic acid-gamma-amides (Acta Chim. Acad. Sci. Hung. 64, 285 /1970/). 4.14 g. of the obtained substance are dissolved in 50 ml. of absolute pyridine, and 9 g. of diphenylphosphoryl chloride are added. The mixture is maintained at 0° C. for 12 hours, then diluted with 80 ml. of chloroform. The separated substance is filtered off, washed with dilute hydrochloric acid and then with water, finally dried in a desiccator over solid potassium hydroxide. The obtained substance is dissolved in 15 ml. of 3.3 molar hydrogen bromide in glacial acetic acid. The solution is allowed to stand for 15 minutes and then it is evaporated in vacuo at 35° C. The residue is dried over solid potassium hydroxide. The dry substance is dissolved in 30 ml. of 1 N sodium hydroxide solution. The mixture is allowed to stand at room temperature for one hour, thereafter acidified to pH 4 with acetic acid, and extracted with 3×30 ml. of ether in order to remove the by-products (phenol and benzyl alcohol). The aqueous phase is passed through a column filled with Dowex 50 ion exchanger (H+cycle), and the column is eluted with water. The eluate is evaporated in vacuo, and the residue is recrystallized from a 2:1 mixture of acetone and water. 0.8 g. of gamma-L-glutamyl-cholamine phosphate are obtained.

EXAMPLE 39

4.68 ml. (50 mmoles) of phosphorous oxychloride are added dropwise to 1.8 ml. of water under cooling and stirring (Biochem. Preparations 6, 76 /1958/), and 1.9 g. (10 mmoles) of gamma-L-glutamyl-cholamine (prepared from carbobenzyloxy-gamma-/α-benzyl/-L-glutamyl-cholamine, see Example 38) are added in small portions to the stirred mixture. The mixture is stirred at 60° C. for 2 hours, then it is allowed to cool, and 0.72 ml. of water are added dropwise to the stirred mixture. The mixture is allowed to stand at room temperature for 2 hours, and then 10 ml. of 96% ethanol and 10 ml. of ether are added dropwise. The reaction mixture is allowed to stand at 4° C. overnight, then 5 ml. of 96% ethanol are added. The separated substance is filtered off, washed with ethanol and ether, and recrystallized from aqueous ethanol. 1.75 g. of gamma-L-glutamyl-cholamine phosphate are obtained.

EXAMPLE 40

4.14 g. (10 mmoles) of carbobenzyloxy-gamma-(α-benzyl)-L-glutamyl-cholamine are dissolved in 40 ml. of pyridine. The solution is cooled to −10° C., and 2.1 g. (11 mmoles) of p-toluenesulfonyl chloride are added in small portions to the vigorously stirred mixture. The mixture is stirred at 0° C. for 3 hours, and then poured onto 40 g. of ice. The separated substance is filtered off, washed with water, and recrystallized from a mixture of ethanol and petroleum ether. The obtained product is subjected to catalytic hydrogenation as described in Example 5. The dry substance obtained after hydrogenation is dissolved in 30 ml. of water, 10.1 g. (40 mmoles) of sodium sulfite heptahydrate are added, the solution is stirred at 40° C. for 24 hours, and finally evaporated in vacuo. The residue is dissolved in a minimum amount of water, the solution is passed through a column filled with Dowex 50 ion exchanger, and the column is eluted with water. The eluate is evaporated in vacuo, and the residue is dried over potassium hydroxide. The crude product is recrystallized from 80% ethanol to yield 1.6 g. of gamma-L-glutamyl-taurine.

EXAMPLE 41

15 ml. of thionyl bromide are added to 4.14 g. (10 mmoles) of carbobenzyloxy-gamma-($\alpha$-benzyl)-L-glutamyl-cholamine, and the mixture is stirred for 3 hours. Thereafter the mixture is diluted with ether, the separated precipitate is filtered off, and recrystallized from a mixture of acetone and petroleum ether. The obtained substance is dissolved in a mixture of dimethyl formamide and water, and 10.1 g. (40 mmoles) of sodium sulfite heptahydrate are added in small portions to the stirred mixture. The mixture is stirred at room temperature for 24 hours and then at 50° C. for 6 hours, and finally filtered. The clear filtrate is evaporated in vacuo, and the residue is subjected to catalytic hydrogenation as described in Example 5. The dry substance obtained after hydrogenation is dissolved in a minimum amount of water, the solution is passed through a column filled with Dowex 50 ion exchanger, and the column is eluted with water. The eluate is evaporated in vacuo, and the residue is recrystallized from 80% ethanol. 1.2 g. of gamma-L-glutamyl-taurine are obtained.

EXAMPLE 42

3.71 g. (10 mmoles) of carbobenzyloxy-L-glutaminic acid-$\alpha$-benzyl ester are dissolved in 60 ml. of acetonitrile. The solution is cooled to $-15°$ C., and 1.4 ml. (10 mmoles) of isobutyl chloroformate and 1.4 ml. (10 mmoles) of triethylamine are added dropwise to the stirred mixture. The mixture is stirred at $-15°$ C. for 30 minutes, and then 2.05 g. (10 mmoles) of bromoethylamine hydrobromide, 1.4 ml. (10 mmoles) of triethylamine and 40 ml. of acetonitrile, cooled to $-15°$ C. are added. The mixture is stirred at $-15°$ C. for 2 hours and then at room temperature for 4 hours. Thereafter the mixture is filtered, and the filtrate is evaporated in vacuo at 35° C. The residue is dissolved in a mixture of dimethyl formamide and water, and 10.1 g. of sodium sulfite heptahydrate are added to the solution. Thereafter one proceeds as described in Example 41 to obtain 1.45 g. of tamma-L-glutamyl-taurine.

EXAMPLE 43

3.02 g. (10 mmoles) of carbobenzyloxy-L-glutamine sodium salt (Liebig's Ann. 640, 145 /1961/) are dissolved in 50 ml. of dimethyl formamide, 12 mmoles of sodium hydride are added in the form of an oily dispersion, and the mixture is heated for 2 hours under exclusion of air humidity. Thereafter a solution of 2.11 g. (10 mmoles) of sodium bromoethanesulfonate in 50 ml. of dimethyl formamide is added dropwise, and the mixture is heated for additional 2 hours. The mixture is evaporated in vacuo. The residue is extracted with ether, then the dry substance is dissolved in water, and the solution is passed through a column filled with Dowex 50 ion exchanger. The column is eluted with water. The eluate is evaporated in vacuo, and the residue is dried over solid potassium hydroxide. The obtained substance is subjected to catalytic hydrogenation as described in Example 5. The product is recrystallized from a mixture of ethanol and water. 1.55 g. of gamma-L-glutamyl-taurine are obtained.

EXAMPLE 44

2.58 g. (10 mmoles) of L-N-(2,6-dioxo-3-piperidyl)-phthalimide (J. Pharm. Sci. 57, 757 /1968/) are dissolved in absolute ethanol containing sodium ethylate. The solution is evaporated in vacuo, the residue is dissolved in 50 ml. of dimethyl formamide, and 2.25 g. (11 mmoles) of sodium bromoethanesulfonate are added to the stirred solution. The mixture is heated for 2 hours, and then it is evaporated in vacuo. The residue is dissolved in water. The solution is passed through a column filled with Dowex 50 ion exchanger, and the column is eluted with water. The eluate is evaporated in vacuo, the residue is admixed with 100 ml. of 0.5 N hydrochloric acid, and the mixture is boiled for 3 hours. The solution is evaporated, 30 ml. of ethanol and 0.7 ml. of 72% hydrazine hydrate are added to the residue, and the obtained mixture is boiled for one hour. Thereafter the mixture is evaporated in vacuo, 25 ml. of 2 N hydrochloric acid are added to the residue, and the mixture is heated first at 50° C. for 10 minutes and then allowed to stand at room temperature for 30 minutes. The separated solid is removed by filtration, the filtrate is evaporated in vacuo, and the residue is dried in a desiccator over solid potassium hydroxide. The obtained substance is dissolved in a 90:8:2 mixture of water, acetic acid and formic acid, and passed through a $2 \times 100$ cm. column filled with Dowex 1 ion exchanger. The ion exchanger has been equilibrated previously with the same solvent mixture. The elution is started with the solvent mixture of the above composition, and 400 ml. of eluate are collected. This fraction contains $\alpha$-L-glutamyl-taurine. Thereafter the column is eluted with 0.5 N hydrochloric acid, and 400 ml. of eluate are collected again. This fraction is evaporated to dryness in vacuo at 35° C. The residue is dried in a desiccator over solid potassium hydroxide and then recrystallized from 80% ethanol. 1.07 g. of gamma-L-glutamyl-taurine are obtained.

EXAMPLE 45

4.43 g. (10 mmoles) of carbobenzyloxy-L-pyroglutaminic acid dicyclohexylammonium salt (Liebig's Ann. 640, 145 /1961/), 1.25 g. (10 mmoles) of taurine and 0.84 g. (10 mmoles) of sodium hydrocarbonate are dissolved in 50 ml. of water. The solution is heated for 4 hours (or allowed to stand at room temperature for 24 hours), and then evaporated in vacuo. The residue is dissolved in water, the solution is passed through a column filled with Dowex 50 ion exchanger, and the column is eluted with water. The eluate is evaporated, and the obtained substance is subjected to catalytic hydrogenation as described in Example 5. The crude product is recrystallized from a mixture of ethanol and water. 2.03 g. of gamma-L-glutamyl-taurine are obtained.

What we claim is:

1. A method of preparing gamma-L-glutamyl taurine which comprises the steps of:
 (a) reacting carbobenzyloxy-L-glutaminic acid-$\alpha$-benzyl ester with a substantially equivalent quantity of triethylamine and a substantially equimolar quantity of isobutylchloroformate, then stirring the reaction mixture with cystamine dihydrochloride, and recovering N,N'-bis-(N-carbobenzyloxygamma-L-glutamyl)-cystamine;
 (b) treating the N,N'-bis-(N-carbobenzyloxygamma-L-glutamyl)-cystamine obtained in step (a) with hydrogen peroxide in lacial acetic acid to produce carbobenzyloxy-gamma-(α-benzyl)-L-glutamyl-taurine;

(c) dissolving the carbobenzyloxy-gamma-(α-benzyl)-L-glutamyl-taurine obtained in step (b) in an alkali hydroxide solution, treating an ion-exchange resin with the resulting solution, eluting said treated resin with water and evaporating the eluate to produce carbobenzyl-gamma-L-glutamyl-taurine; and (d) subjecting the carbobenzyloxy-gamma-L-glutamyl-taurine to acidolysis to produce gamma-L-glutamyl-taurine.

2. The method defined in claim 1 wherein step (d) is carried out by treatment of the carbobenzyloxy-gamma-L-glutamyl-taurine with hydrogen bromide in glacial acetic acid.

3. The method defined in claim 1 wherein step (c) is carried out by dissolving the carbobenzyloxy-gamma-(α-benzyl)-L-glutamyl taurine in a potassium hydroxide solution.

* * * * *